(12) United States Patent
Ralston et al.

(10) Patent No.: US 6,245,548 B1
(45) Date of Patent: Jun. 12, 2001

(54) ACTIVATION OF PURE PROTHROMBIN TO THROMBIN WITH ABOUT 30% TO ABOUT 40% SODIUM CITRATE

(75) Inventors: Annemarie H. Ralston, Bethesda, MD (US); William N. Drohan, Springfield, VA (US)

(73) Assignee: American National Red Cross, Falls Church, VA (US)

( * ) Notice: Subject to any disclaimer, the term of this patent is extended or adjusted under 35 U.S.C. 154(b) by 0 days.

(21) Appl. No.: 09/522,010

(22) Filed: Mar. 9, 2000

(51) Int. Cl.[7] .............................. C12N 9/74; A61K 38/48
(52) U.S. Cl. ........................................ 435/214; 424/94.64
(58) Field of Search ........................ 435/214; 424/94.64

(56) References Cited

PUBLICATIONS

Rossi et al., C. R. Acad. Sc. Paris., No. 2, vol. 268, pp. 418–419, 1969.*
Lanchantin et al., Journal of Biological Chemistry, vol. 240, No. 8, pp. 3276–3282, 1965.*
Cole et al., Canadian Journal of Biochemistry, vol. 44, No. 7, pp. 1051–1059, 1966.*
Cole, Thromb. Diath. Haemorrh., vol. 19, No. 3–4, pp. 321–333, 1968.*
Heldebrandt et al., Journal of Biological Chemistry, vol. 248, No. 10, pp. 3642–3652, 1973.*

* cited by examiner

*Primary Examiner*—David M. Naff
*Assistant Examiner*—Michael V. Meller
(74) *Attorney, Agent, or Firm*—Burns, Swecker & Mathis, L.L.P.

(57) ABSTRACT

A method for the production of thrombin from pure prothrombin is provided by converting pure prothrombin by treating pure prothrombin with sodium citrate in the absence of additional coagulation factors. Preferably, a solution is used containing about 30% to about 40% sodium citrate.

6 Claims, No Drawings

ACTIVATION OF PURE PROTHROMBIN TO THROMBIN WITH ABOUT 30% TO ABOUT 40% SODIUM CITRATE

FIELD OF THE INVENTION

The present invention relates to a novel method for the production of thrombin. More specifically, the present invention relates to a method for converting pure prothrombin or prothrombin free of other coagulating factors to thrombin by treating prothrombin with sodium citrate.

BACKGROUND OF THE INVENTION

The blood clotting cascade is activated when there is a change in the integrity of the blood circulatory system which results in the escape of blood. Generally, circulating platelet collect at the site of the wound, and upon exposure to air, the platelets rupture releasing the serine protease thromboplastin (Factor III). In the presence of vitamin K, $Ca^{++}$ ions and several other essential factors, thromboplastin catalyzes the conversion of prothrombin (Factor II) to thrombin, a serine protease with a molecular weight ranging from 36 kDa to 37 kDa. The newly formed thrombin catalyzes the hydrolysis of fibrinogen to form fibrin strands. The resulting fibrin in combination with activated platelets form a plug or clot to seal the wound, and contraction of the clot pulls the wound together preventing further bleeding (Clegg et al., Advanced biology principle and applications. London: John Murray Publishers, Ltd. (1994); Wallace et al., Biology: The science of life. Scott, Foresman and Company (1986)).

Thrombin can be formed from prothrombin in vitro by three known processes. One process involves incubating prothrombin with isolated thromboplastin in the presence of calcium chloride. This process is described, for example, in EP 0439156A. The disadvantage of using this method is that the thromboplastin typically employed is extracted from bovine lungs. The extraction process is time consuming and the resulting bovine thromboplastin can be contaminated with viruses or bacteria which carries the risk of transmitting infectious diseases. In addition, trace amounts of bovine thromboplastin that might be present in the resulting purified thrombin can cause immunological reactions in the host receiving thrombin produced by this method.

Another in vitro process for converting prothrombin to thrombin involves treating a mixture of prothrombin, Factor Xa, Factor Va and phospholipids with calcium ions. This process is described, for example, in U.S. Pat. Nos. 5,219,995 and 5,907,032. According to U.S. Pat. No. 5,907,032, the prothrombin mixture may also contain additional clotting factors, such as Factor X, Factor V, Factor IX, Factor IXa and trace amounts of thrombin. Thrombin produced in this manner has a specific activity ranging from about 250–700 U/mg. The requirement for additional clotting factors and the low specific activity are undesirable features of this process.

Similarly, in other processes, purified prothrombin is treated with activated Factor X, Factor V, phospholipid and calcium ions under physiological conditions to yield thrombin, or purified prothrombin is treated with 25% sodium citrate in the presence of coagulation factors such as Factor VIII, Factor IX and Factor X (Seegers, W. H., Proc. Soc. Exp. Biol. Med., 72:677–80, 1949; Teng et al., Thrombosis Research, 22:203–12, 1981). The authors suggest that one or more of the various coagulating factors play a vital role in the process. Again, the requirement for additional clotting factors renders this process undesirable and inconvenient.

Still another in vitro process requires the use of snake venom to convert prothrombin to thrombin (Denson et al. Toxicon, 7(1):5–11, 1969; Masci et al. Biochem. Int., 17(5):825–35, 1988; Rosing et al. Toxicon, 30(12):1515–27, 1992; Stocker et al. Toxicon, 32(10):1227–36, 1994). Snake venoms are classified into four groups based on their structure and function. Group I venoms convert prothrombin to an intermediate meizothrombin. Group II and III venoms cleave peptide bonds in prothrombin to produce thrombin. However, both Group II and III venoms require additional factor such as phospholipids, Factor Va and $CaCl_2$. Group IV venoms convert prothrombin to an inactive form of thrombin (Rosing et al., Toxicon, 30(12):1515–27, 1992). The disadvantages to using snake venom are 1) it is difficult to obtain snake venom in large quantities, 2) some forms of snake venom convert prothrombin into enzymatically inactive forms of thrombin, and 3) traces of snake venom in thrombin preparation can be extremely harmful to the patient.

As discussed above, thrombin is an essential component of blood coagulation that acts during the final stages of the blood clotting process. Due to this function, thrombin is used clinically as a styptic agent. Additionally, thrombin functions as an activator of protein C, Factor V, platelets and proteins of the complement system. Thus, it is desirable to develop processes whereby thrombin can be easily produced and readily available. However, until now, there have been no commercially viable methods to efficiently and simply produce thrombin from pure prothrombin. Moreover, there have been no methods whereby workers could convert prothrombin to thrombin in the absence of coagulating factors or other activating enzymes. Accordingly, there is a need in the art for an efficient and simple non-enzymatic method for producing thrombin from pure prothrombin in the absence of additional coagulation factors.

SUMMARY OF THE INVENTION

To satisfy the need for an efficient and simple non-enzymatic method for producing thrombin and to avoid the numerous drawbacks of the methods described above, the inventors have developed a method for preparing enzymatically active thrombin from pure prothrombin. Specifically, the present invention provides a novel method for producing thrombin comprising treating pure isolated or recombinant prothrombin with sodium citrate.

DETAILED DESCRIPTION OF THE INVENTION

Prior to describing the preferred embodiments, the following definitions are provided.

Host

A host includes humans, non-human primates, non-human mammals, and ungulates. Especially included are agricultural animals, and domestic animals, such as dogs and cats.

Pure Prothrombin

Pure prothrombin is prothrombin in the absence of other coagulation factors. Pure prothrombin includes recombinant prothrombin.

As discussed, the present invention is broadly directed to a method of producing thrombin from prothrombin. Based on the teachings of the prior art, one would expect that the in vitro production of thrombin from prothrombin is a time consuming and inefficient process which requires the presence of additional coagulation factors. The inventors, however, have made the surprising and unexpected discovery that thrombin can be produced efficiently and simply from pure prothrombin under non-physiological and non-enzymatic conditions, i.e., the conversion takes place in the absence of additional coagulation factors.

In accordance with one embodiment of the invention, there is provided a method for producing thrombin from pure prothrombin. The method comprises incubating a sample of prothrombin with sodium citrate and determining the presence of thrombin activity.

One of skill in the art will appreciate that prothrombin can be obtained from various sources such as blood or blood fractions, plasma or cryoprecipitated plasma. It is a preferred embodiment of the invention to utilize purified prothrombin, however, other forms of prothrombin are encompassed by the present invention. For example, depending on the host being treated, isolated prothrombin or recombinant prothrombin can be used. In a more preferred embodiment, purified human prothrombin is used.

In another preferred embodiment of the invention, prothrombin is incubated with sodium citrate to produce thrombin. Prothrombin is incubated with sodium citrate which is present in an amount ranging from greater than about 25% to about 45%. Preferably, the sodium citrate is present in an amount ranging from about 30% to about 40%. In an even more preferred embodiment, the concentration of sodium citrate is about 35%.

The requirement for additional clotting factors during the conversion from prothrombin to thrombin is undesirable and inconvenient especially for the large-scale production of thrombin where large amounts of clotting factors will be needed. Therefore, in another embodiment of the invention, the conversion from pure prothrombin to thrombin is carried out in the absence of additional coagulation factors.

In accordance with another embodiment of the present invention, the incubation of pure prothrombin with sodium citrate occurs at a temperature ranging from about 20° C. to about 40° C. and for a period of time ranging from about 16 hours to about 30 hours. In a more preferred embodiment, the incubation temperature is 37° C. and the incubation period ranges from about 24 to about 28 hours.

It is an unexpected and advantageous feature of the present invention that prothrombin can be activated non-enzymatically. Specifically, by resort to the present process, one can activate prothrombin in the absence of various coagulation factors, notably Factor VIII, Factor IX, Factor X and Factor XIII. Until the advent of this process, it was thought that one or more of those coagulation factors were essential to the activation of prothrombin. Thus, the present invention affords a means for activating prothrombin in the absence of one or more of Factor VIII, Factor IX, Factor X, Factor XIII, or other coagulation factors commonly associated with the coagulation pathway.

Having described the preferred embodiments of the present invention, one skilled in the art will recognize that modifications can be made to the preferred embodiments without altering the scope of the invention.

The following examples are provided to further describe the invention, however, the scope of the invention is not limited thereby.

EXAMPLES

Example I

Activation of Prothrombin

For the activation of prothrombin to form thrombin, source material containing prothrombin was obtained from the flow through fraction after the application of plasma to a protein C monoclonal antibody affinity column. This plasma derived flow through is rich in vitamin K-dependent proteins and contained 1% Triton X-100, 0.3% TnBP, 0.3% Tween 80 (w/v). Before the prothrombin (FII) of this source can be activated with sodium citrate at pH 7.0, it has to undergo two precipitations with polyethylene glycol (PEG). In the first PEG precipitation at 15% PEG (w/v) inhibitors of the prothrombin activation are removed quantitatively. The prothrombin, collected in the second PEG precipitation at 20% (w/v), was subsequently activated with sodium citrate.

Briefly, prothrombin was incubated with sodium citrate at a concentration of 35%(w/v). Activation of the 20% PEG precipitate with $CaCl_2$ (40 mM) was not possible. The conversion of prothrombin to thrombin occurs best within 26–28 hours at 37° C. at sodium citrate concentration of 35% (w/v).

The thrombin was purified subsequently chromatographically on a SP-Sephrarose column. The specific activity of the thrombin ranged from 1000 IU to 1800 IU/mg. This is considerably higher than thrombin prepared in accordance with U.S. Pat. No. 5,304,372 (specific activity of 20–40 U/mg) and U.S. Pat. No. 5,907,032 (specific activity of 250–700 U/mg).

Two phases are observed during activation. After an initial lag period, thrombin activity develops exponentially until it reachers a plateau, which is followed by a second phase of progressive thrombin autolysis. The first activation intermediate appears to be meizothrombin, followed at later activation times by FXa like activity, as determined by Amidoblot Technics. Conversion of prethrombin-2 to α-thrombin was normally completed after 26–28 hours. If reaction is not stopped at this point, complete degradation of α-thrombin to β- and γ-thrombin will occur by thrombin autolysis.

Activation of prothrombin with EDTA, $MgCl_2$, Poly Aspartic Acid did not lead to thrombin.

Products of the method of the present invention were successfully applied for the thrombin activation of protein C (PC) to APC (Orthner et al., Vox. Sang., 69:309–18 (1995)).

Example II

Comparison of Calcium Chloride and Sodium Citrate Activation of Pure Prothrombin The activation was performed with purified prothrombin (FII) (Lot 29018006; FIX by-product, received from S. Miekka) at FII concentrations of 5–10 mg/ml of saline or phosphate buffer. This material might still contain trace amounts of coagulation factors. Activation was performed at 37° C. and pH 6.5–7.5. The salts were added as solids to the FII solution and gently rotated during the incubation. The development of the thrombin activity was monitored with substrate S-2238 (a highly specific substrate used to identify thrombin activity), and the activity was compared to thrombin activity obtained by activation with Echis carinatus. SDS-PAGE analysis was used to verify the conversion of prothrombin to α-thrombin, as well as its activation and degradation products.

Substrate S-2238 is being cleaved by α-, β-, and γ-thrombin. To distinguish between α-thrombin and γ-thrombin which does not clot fibrinogen, we used a fibrinogen clotting assay to confirm presence of α-thrombin.

Calcium chloride did not activate prothrombin to thrombin, however, sodium citrate at a concentration of 35% (w/v) activated prothrombin to thrombin.

Example III

Activation of Prothrombin to Thrombin by Polyglutamic Acid

Activation of prothrombin was carried out in a manner similar to that described above. Briefly, purified prothrombin was incubated with 2% (w/v) Poly Glutamic Acid at 37° C. and pH 6.5–7.5. The development of the thrombin activity was monitored with substrate S-2238, and the activity was compared to thrombin activity obtained by activation with Poly Aspartic Acid. SDS-PAGE analysis was used to verify the conversion of prothrombin to α-thrombin, as well as its activation and degradation products. To distinguish between α-thrombin and γ-thrombin which does not clot fibrinogen, we used a fibrinogen clotting assay to confirm presence of α-thrombin. Activation of prothrombin with 2% Poly Glutamic Acid progresses at a slow rate and appears to lead preferably to β-thrombin which also can convert fibrinogen to fibrin. Activation of prothrombin with Poly Aspartic Acid did not result in thrombin formation.

We assumed that the activation of purified prothrombin was unlikely to be possible in the absence of other plasma coagulation proteins. However, we could determine that conversion of prothrombin to thrombin was possible after prolonged incubation at 37° C. in the presence of sodium citrate and polyglutamic acid (2%). Conversion in the presence of calcium did not occur. The activation products of the sodium citrate and polyglutamic acid activations were capable to clot fibrinogen.

The activation of purified prothrombin at 35% sodium citrate concentration is faster and the conversion of prethrombin-2 is complete. Degradation and autolysis of α-thrombin to β- and γ-thrombins is better controlled at 35% (1.19M), than at 25% sodium citrate (0.85M). Activation of prothrombin with polyglutamic acid was observed after 45 hours at 37° C. β-thrombin appears to be the main activation product with polyglutamic acid (2%). β-thrombin can also convert fibrinogen to fibrin.

Summary of Activation Results of Various Prothrombin Sources With Polyglutamic Acid

TABLE I

|  | Activation @ 25% (w/v) Sodium Citrate | Activation @ 35% (w/v) Sodium Citrate | Activation @ 2% (w/v) of Poly Glutamic Acid |
|---|---|---|---|
| Prothrombin Prepared from Mass Capture | ++ | ++++ | ND |
| Purified Prothrombin | + | ++++ | + |
| Recombinant Prothrombin | Negative | ++++ | ND |

Example IV

Activation of Recombinant Prothrombin to Thrombin by Sodium Citrate

The activation of recombinant prothrombin (rFII) (Cohesion, Palo Alto Calif.) could only be converted to thrombin (rFIIa) using 35% (w/v) sodium citrate concentrations. At sodium citrate concentrations of 25% (w/v) no conversion was obtained after 32 hours at 37° C., which is in contrast to the previous observations with plasma-derived prothrombin.

To achieve the conversion, solid sodium citrate was added to the recombinant prothrombin solution and gently rotated at 37° C. Time samples were taken and the S-2238 hydrolysing activity was monitored over a time period of 32 hours. Clotting activity was observed after 22 hours. The conversion was evaluated by SDS-PAGE and S-2238 amidolytic analysis.

Conclusion:

Sodium citrate activation of recombinant prothrombin results in thrombin formation. The resulting product can clot purified fibrinogen.

All references cited herein are hereby incorporated by reference in their entirety.

What is claimed is:

1. A method for producing thrombin comprising incubating pure prothrombin in a solution of about 30% to about 40% sodium citrate in the absence of any other blood coagulation factors.

2. A method for activating prothrombin to thrombin comprising incubating pure prothrombin in a solution of about 30% to about 40% sodium citrate.

3. A method for activating prothrombin to thrombin comprising incubating pure prothrombin in a solution of about 35% sodium citrate for about 26 to about 28 hours at a temperature of about 20° to about 40° C.

4. The method according to claim 1, wherein said pure prothrombin is recombinant prothrombin.

5. The method according to claim 4, wherein said recombinant prothrombin is human.

6. The method according to claim 1, wherein said pure prothrombin is pure human prothrombin.

\* \* \* \* \*